United States Patent [19]

Ponpipom

[11] 4,301,152

[45] Nov. 17, 1981

[54] IMMUNOLOGIC ADJUVANT

[75] Inventor: Mitree M. Ponpipom, Branchburg, N.J.

[73] Assignee: Merck & Co., Inc., Rahway, N.J.

[21] Appl. No.: 88,692

[22] Filed: Oct. 26, 1979

[51] Int. Cl.$^3$ .......................... A61K 31/575; C07J 9/00
[52] U.S. Cl. ........................................ 424/182; 536/5; 536/18; 536/53; 536/122
[58] Field of Search ..................... 536/5, 53, 122, 18; 424/182

[56] References Cited

U.S. PATENT DOCUMENTS 2,216,617  10/1940  Katz ........................................ 536/53
4,131,732  12/1978  Hill et al. ............................... 536/122
4,189,471   2/1980  Ponpipom et al. ..................... 424/182

OTHER PUBLICATIONS

Noller, "Chemistry of Organic Compounds", 3rd Ed., W. B. Saunders Co., Phila., Pa., p. 604.
Behling et al., "Jour. of Immunology", vol. 117, No. 3, Sep. 1976, pp. 847–851.

*Primary Examiner*—Johnnie R. Brown
*Attorney, Agent, or Firm*—Donald J. Perrella; Hesna J. Pfeiffer

[57] ABSTRACT

Immunologic adjuvants are obtained by the synthesis of 6-(5-cholesten-3β-yloxy)hexyl 6-amino-6-deoxy-1-thio-β-D-galactopyranoside and its 6-deoxy-6-oleamido derivative.

9 Claims, No Drawings

IMMUNOLOGIC ADJUVANT

BACKGROUND OF THE INVENTION

The present invention relates to an immunologic adjuvant and, more particularly, to novel glycolipid immunologic adjuvant and to improved vaccine formulations containing a novel glycolipid immunologic adjuvant.

Broadly considered, the vaccines utilized at the present time are "fluid vaccines." The term "fluid vaccine" designates a suspension of an immunogenic or desensitizing agent in water or in a medium comprising a single, aqueous, liquid phase. The principal purpose for employment of an immunologic adjuvant is to achieve a more durable immunity of a higher level employing a smaller antigenic mass in a fewer number of doses than could be achieved by administration of the equivalent aqueous antigen. It may be noted that development of an immunologically satisfactory and pharmacologically acceptable adjuvant is a prime essential for the preparation of workable multivalent killed virus vaccines which are effective and practical in the prevention of viral, bacterial, mycoplasmal, or rickettsial diseases.

OBJECTS OF THE INVENTION

It is an object of the present invention to provide new glycolipid compounds. Another object is to provide methods for preparing these glycolipid compounds. A further object is to provide vaccine compositions containing these glycolipid compounds. These and other objects of the present invention will be apparent from the following description.

SUMMARY OF THE INVENTION

Carbohydrate derivatives having the following formulae:

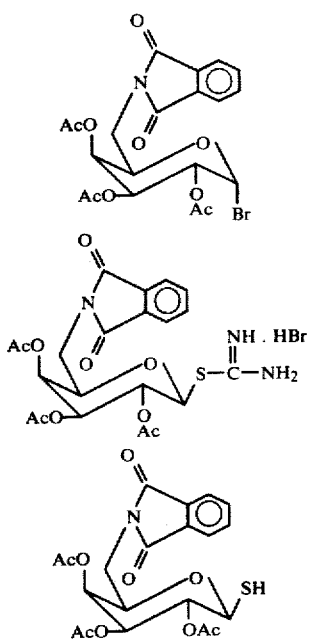

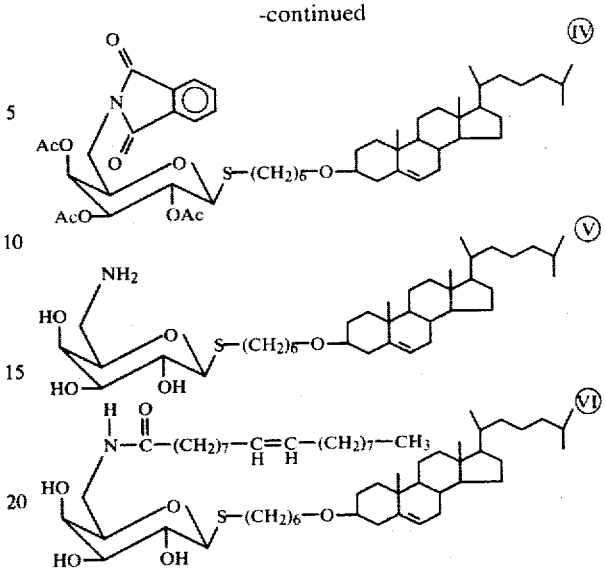

are useful immunologic adjuvants in vaccines or are useful as intermediates in their preparation. Compounds I, II, III, and IV are intermediates in the production of immunologic adjuvants. Compound V is both an intermediate and is useful as an immunologic adjuvant in the production of other adjuvants; and compound VI is useful as an immunologic adjuvant.

DETAILED DESCRIPTION OF THE INVENTION

The glycolipid compounds of the present invention, which are useful as immunologic adjuvants, are synthesized from the known compound 6-deoxy-1,2:3,4-di-O-isopropylidene-6-phthalimido-α-D-galactose. This compound is prepared in one method of operation by the reaction of potassium phthalimide and 6-deoxy-6-iodo-1,2:3,4-di-O-isopropylidene-α-D-galactose. Following the reaction, the mixture is separated by column chromatography, and the product is recrystallized from methanol. The next step of the synthesis involves the reaction of 6-deoxy-1,2:3,4-di-O-isopropylidene-6-phthalimido-α-D-galactose in aqueous acetic acid to produce the corresponding 6-deoxy-6-phthalimido-D-galactopyranose, which is readily provided by recrystallization from alcohol.

The compounds produced in this manner, as well as the compound used as starting material, are reported in the literature and are known compounds; cf., Veksler, ZH. OBSHCH. KHIM., 36, 2102-5 (1966).

The first new intermediate prepared in connection with the present synthesis is obtained by the acetylation of 6-deoxy-6-phthalimido-D-galactopyranose, resulting in the production of 1,2,3,4-tetra-O-acetyl-6-deoxy-6-phthalimido-D-galactopyranose. This tetra-O-acetyl compound is then treated in a halogenated hydrocarbon solvent, for example dichloromethane, with hydrobromic acid in glacial acetic acid to produce the compound 2,3,4-tri-O-acetyl-6-deoxy-6-phthalimido-α-D-galactopyranosyl bromide. The resulting pyranosyl bromide is then reacted with thiourea under substantially anhydrous conditions to produce the corresponding 2-thiopseudourea compound, which is cleaved to the corresponding 1-thio compound by treatment with aqueous potassium metabisulfite solution. The thio compound thus produced is then condensed in the presence of an amine with 6-(5-cholesten-3β-yloxy)hexyl iodide to produce 6-(5-cholesten-3β-yloxy)hexyl 2,3,4-tri-O-hexyl-6-deoxy-6-phthalimido-1-thio-β-D-galactopyranoside. The resulting cholesten derivative is then hydrolyzed under mild conditions to produce the deacylated amino-galactopyranoside, i.e., 6-(5-cholesten-3β-yloxy)hexyl 6-amino-6-deoxy-1-thio-β-D-galactopyranoside. This compound is not only useful as an intermediate in the preparation of immunologic adjuvants, but is also useful in and of itself as an immunologic adjuvant.

Said amino-galactopyranoside compound is then acylated with oleic acid to produce the corresponding 6-oleic amino compound, i.e., 6-(5-cholesten-3β-yloxy)-hexyl 6-deoxy-6-oleamido-1-thio-β-D-galactopyranoside.

The novel adjuvants of the invention may be employed to potentiate the antibody response of antigenic materials. The term "antigen" and "antigenic material" which are used interchangeably herein include one or more non-viable immunogenic or desensitizing (antiallergic) agents of bacterial, viral, or other origin. The antigen component of the products of the invention may consist of a dried powder, an aqueous solution, an aqueous suspension and the like, including mixtures of the same, containing a non-viable immunogenic or desensitizing agent or agents.

The aqueous phase may conveniently be comprised of the antigenic material in a parenterally acceptable liquid. For example, the aqueous phase may be in the form of a vaccine in which the antigen is dissolved in a balanced salt solution, physiological saline solution, phosphate buffered saline solution, tissue culture fluids, or other media in which the organism may have been grown. The aqueous phase also may contain preservatives and/or substances conventionally incorporated in vaccine preparations. The adjuvant emulsions of the invention may be prepared employing techniques well known to the art.

The antigen may be in the form of purified or partially purified antigen derived from bacteria, viruses, rickettsia or their products, or extracts of bacteria, viruses, or rickettsia; or the antigen may be an allergen such as pollens, dusts, danders, or extracts of the same; or the antigen may be in the form of a poison or a venom derived from poisonous insects or reptiles. In all cases, the antigens will be in the form in which their toxic or virulent properties have been reduced or destroyed and which when introduced into a suitable host will either induce active immunity by the production therein of antibodies against the specific microorganisms, extract, or products of microorganisms used in the preparation of the antigen, or, in the case of allergens, they will aid in alleviating the symptoms of the allergy due to the specific allergen. The antigens can be used either singly or in combination, for example, multiple bacterial antigens, multiple viral antigens, multiple mycoplasmal antigens, multiple rickettsial antigens, multiple bacterial or viral toxoids, multiple allergens or combinations of any of the foregoing products can be combined in the aqueous phase of the adjuvant composition of this invention. Antigens of particular importance are derived from bacteria such as B. pertussis, Leptospira pomona, and icterohaemorrhagiae, S. paratyphi A and B, C. diphtheriae, C. tetani, C. botulinum, C. perfringens, C. feseri, and other gas gangrene bacteria, B. anthracis, P. pestis, P. multocida, V. cholerae, Neisseria meningitidis, N. gonorrheae, Hemophilus influenzae, Treponema pollidum, and the like; from viruses as polio virus (multiple types), adeno virus (multiple types), parainfluenza virus (multiple types), measles, mumps, respiratory syncytial virus, influenza (various types), shipping fever virus (SF$_4$), Western and Eastern equine encephalomyelitis, Japanese B. encephalomyelitis, Russian Spring Summer encephalomyelitis, hog cholera virus, Newcastle disease virus, fowl pox, rabies, feline and canine distemper and the like viruses, from rickettsiae as epidemic and endemic typhus or other members of the spotted fever group, from various spider and snake venoms or any of the known allergens, for example, from ragweed, house dust, pollen extracts, grass pollens, and the like.

The following examples illustrate the present invention without, however, limiting the same thereto.

EXAMPLE 1

6-Deoxy-1,2:3,4-di-O-isopropylidene-6-phthalimido-α-D-galactose

Potassium phthalimide (4.94 g.) is added to a solution of 6-deoxy-6-iodo-1,2:3,4-di-O-isopropylidene-α-D-galactose (9.0 g.) in N,N-dimethylformamide (50 ml.). The suspension is heated with stirring for 8 hours at 130° C. (bath temperature). Another batch of potassium phthalimide (1.25 g.) is added to the cooled brown solution which is then heated with stirring for another 8 hours at the same temperature. The solution is evaporated in vacuo to a dark syrup which is partitioned between ethyl ether and water. The dark insoluble material is filtered and discarded, and the ethereal layer is washed three times with water, dried, and evaporated to a syrup (consisting of the product and the starting material). This mixture is separated by column chromatography on silica gel with 5% ethyl acetate in chloroform as eluant. The title compound is isolated as a crystalline material which is recrystallized from methanol to give 5.1 g. (54%) of the product, m.p., 138°–141° C.; [lit. m.p. 144.5°–145.5° C.]; n.m.r. (chloroform-d): δ 5.42 (d, J$_{1,2}$ 5.0 Hz, H-1), 7.47–7.82 (4 aromatic), 1.23, 1.37, 1.43, and 1.52

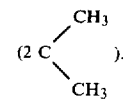

EXAMPLE 2

6-Deoxy-6-phthalimido-D-galactopyranose

A solution of 6-deoxy-1,2:3,4-di-O-isopropylidene-6-phthalimido-α-D-galactose (5.0 g.) in glacial acetic acid (50 ml.) and water (18 ml.) is heated for 32 hours at 80° C. (bath temperature). The solution is filtered and the filtrate is evaporated in vacuo to a crystalline mass. Recrystallization from absolute ethanol affords the title compound (3.0 g., 76%), m.p. 155° C. (dec.), softened at 95° C.

EXAMPLE 3

Step A:

1,2,3,4-Tetra-O-acetyl-6-deoxy-6-phthalimido-D-galactopyranose

6-Deoxy-6-phthalimido-D-galactopyranose (2.9 g.) is acetylated with acetic anhydride (12 ml.) in pyridine (20 ml.) in the normal manner to give 1,2,3,4-tetra-O-acetyl- 6-deoxy-6-phthalimido-D-galactopyranose (4.30 g., 96%) as a mixture of α- and β-anomers in the ratio of 1:1.6, $[\alpha]_D^{27}$ +52.5° C. (C 1.0, chloroform); n.m.r. (chloroform-d): δ 5.70 (d, $J_{1,2}$ 8.0 Hz, H-1β), 6.33 (b, H-1α).

Step B:
2,3,4-Tri-O-acetyl-6-deoxy-6-phthalimido-α-D-galactopyranosyl bromide A solution of 1,2,3,4-tetra-O-acetyl-6-deoxy-phthalimido-D-galactopyranose (4.2 g.) in dichloromethane (2 ml.) is treated with 30-32% hydrobromic acid in glacial acetic acid (10 ml.) for 1 hour. The reaction mixture is poured into ice-water, and the product is immediately extracted with dichloromethane. The organic layer is washed with cold aqueous sodium hydrogencarbonate and cold water, dried, and evaporated in vacuo to give the title compound as a syrup (4.0 g., 91%); n.m.r. (chloroform-d); δ 6.63 (d, $J_{1,2}$ 4.0 Hz, H-1), 7.58-7.90 (4 aromatic), 1.96, 2.07, and 2.13 (3 OAc).

EXAMPLE 4
2,3,4-Tri-O-acetyl-6-deoxy-6-phthalimido-1-thio-β-D-galactopyranose (A) A solution of 2,3,4-tri-O-acetyl-6-deoxy-6-phthalimido-α-D-galactopyranosyl bromide (4.0 g.) and thiourea (0.67 g.) in dry acetone (20 ml.) is heated under reflux for 4 hours. The solution is evaporated in vacuo to a syrup which is partitioned between water and dichloromethane. The organic layer is reextracted with water three times. The combined aqueous extracts are evaporated to give 2-S-(2,3,4-tri-O-acetyl-6-deoxy-6-phthalimido-β-D-galactopyranosyl)-2-thiopseudourea (3.40 g.).

(B) Chloroform (9.0 ml.) is added to a solution of 2-S-(2,3,4-tri-O-acetyl-6-deoxy-6-phthalimido-β-D-galactopyranosyl)-2-thiopseudourea (3.4 g.) in water (10 ml.) containing potassium metabisulfite (1.38 g.). The mixture is heated with stirring under reflux for 15 minutes. The cooled solution is separated, and the organic layer is dried and evaporated in vacuo to give the title compound (2.5 g.). This material is used directly for the preparation of 6-(5-cholesten-3β-yloxy)hexyl 2,3,4-tri-O-acetyl-6-deoxy-6-phthalimido-1-thio-β-D-galactopyranoside.

EXAMPLE 5
6-(5-Cholesten-3β-yloxy)hexyl 2,3,4-tri-O-acetyl-6-deoxy-6-phthalimido-1-thio-β-D-galactopyranoside Triethylamine (0.8 ml.) is added to a solution of 2,3,4-tri-O-acetyl-6-deoxy-6-phthalimido-1-thio-β-D-galactopyranose (2.5 g.) and 6-(5-cholesten-3β-yloxy)hexyl iodide (3.3 g.) in dichloromethane (20 ml.). The solution is kept at room temperature under nitrogen overnight, and washed with water, dried, and evaporated in vacuo to a syrup (4.71 g.). This material is put on a column of silica gel and eluted with chloroform followed by 2% ethyl acetate in chloroform. The desired fractions are combined and evaporated in vacuo to give the title compound (4.0 g., 78%); $R_f$ 0.2 (CHCl$_3$-EtOAc. 95:5), $[\alpha]_D^{27}$ −93° C. (C 1.18, chloroform); n.m.r. (chloroform-d); δ 7.60-7.91 (4 aromatic), 1.93, 2.03, and 2.24 (3 OAc) 0.68 (CH$_3$-18).

EXAMPLE 6
6-(5-Cholesten-3β-yloxy)hexyl 6-amino-6-deoxy-1-thio-β-D-galactopyranoside A suspension of 6-(5-cholesten-3β-yloxy)hexyl 2,3,4-tri-O-acetyl-6-deoxy-6-phthalimido-1-thio-β-D-galactopyranoside (710 mg.) in methanol (10 ml.) and n-butylamine (10 ml.) is heated under reflux for 16 hours. The solution is evaporated to a crystalline mass. Chloroform is added and the solid is filtered and washed with chloroform. The combined filtrates are evaporated to a syrup which is put on a column of silica gel and eluted with chloroform-methanol-ammonium hydroxide (80:20:2). The desired fractions are combined and evaporated to a syrup which is triturated with ethyl ether to give crystals (390 mg. 76%); $R_f$ 0.28 (CHCl$_3$-MeOH-NH$_4$OH, 80:20:2), $[\alpha]_D^{27}$ −29.5° C. (C 1.05, chloroform), m.s.: m/e 665 (M$^+$ +1).

EXAMPLE 7
6-(5-Cholesten-3β-yloxy)hexyl 6-deoxy-6-oleamido-1-thio-β-D-galactopyranoside A solution of dicyclohexylcarbodiimide (106 mg.) in chloroform (5 ml.) is added to a solution of 6-(5-cholesten-3β-yloxy)hexyl 6-amino-6-deoxy-1-thio-β-D-galactopyranoside (309 mg.) and oleic acid (131.5 mg.) in chloroform (20 ml.). After 3 hours at room temperature, the reaction mixture is filtered and washed with water (20 ml.) and methanol (25 ml.). The organic layer is dried and evaporated in vacuo to a syrup which is crystallized from methanol to give the title compound (238 mg., 55%); m.p. 160°-163° C., $[\alpha]_D^{27}$ −5.0° C. (C 1.0, chloroform).

Anal Calc. for C$_{57}$H$_{101}$NSO$_6$: C, 73.73; H, 10.96; N, 1.51; S, 3.45. Found: C, 73.75; H, 11.32; N, 1.45; S, 3.27.

What is claimed is:

1. An intermediate in the preparation of 6-(5-cholesten-3β-yloxy)hexyl 6-amino-6-deoxy-1-thio-β-D-galactopyranoside selected from the group consisting of 1,2,3,4-tetra-O-acetyl-6-deoxy-6-phthalimido-D-galactopyranose; 2,3,4-tri-O-acetyl-6-deoxy-6-phthalimido-α-D-galactopyranosyl bromide; 2,3,4-tri-O-acetyl-6-deoxy-6-phthalimido-1-thio-β-D-galactopyranose; or 6-(5-cholesten-3β-yloxy)hexyl 2,3,4-tri-O-acetyl-6-deoxy-6-phthalimido-1-thio-β-D-galactopyranoside.

2. A compound of claim 1 having the name 1,2,3,4-tetra-O-acetyl-6-deoxy-6-phthalimido-D-galactopyranose.

3. A compound of claim 1 having the name 2,3,4-tri-O-acetyl-6-deoxy-6-phthalimido-α-D-galactopyranosyl bromide.

4. A compound of claim 1 having the name 2,3,4-tri-O-acetyl-6-deoxy-6-phthalimido-1-thio-β-D-galactopyranose.

5. A compound of claim 1 having the name 6-(5-cholesten-3β-yloxy)hexyl 2,3,4-tri-O-acetyl-6-deoxy-6-phthalimido-1-thio-β-D-galactopyranoside.

6. An immunologic adjuvant compound selected from 6-(5-cholesten-3β-yloxy)hexyl 6-amino-6-deoxy-1-thio-β-D-galactopyranoside and the corresponding oleic acid amide thereof.

7. A compound according to claim 6 having the name 6-(5-cholesten-3β-yloxy)hexyl 6-amino-6-deoxy-1-thio-β-D-galactopyranoside.

8. A compound according to claim 6 having the name 6-(5-cholesten-3β-yloxy)hexyl 6-deoxy-6-oleamido-1-thio-β-D-galactopyranoside.

9. A composition comprising a compound of claim 6 in an amount effective to exert an adjuvant effect and a pharmaceutically acceptable carrier.

* * * * *